United States Patent [19]

Imai

[11] Patent Number: 5,932,700

[45] Date of Patent: Aug. 3, 1999

[54] PROTEIN INHIBITING THE GROWTH OF HUMAN ENDOMETRIAL FIBROBLASTS

[75] Inventor: Atsushi Imai, Gifu-ken, Japan

[73] Assignee: Suntory Limited, Japan

[21] Appl. No.: 08/920,872

[22] Filed: Aug. 29, 1997

Related U.S. Application Data

[63] Continuation of application No. 08/317,461, Oct. 4, 1994, abandoned.

[30] Foreign Application Priority Data

Oct. 5, 1993 [JP] Japan .................................. 5-249355

[51] Int. Cl.⁶ ........................... C07K 17/00; C12P 21/04; G01N 33/48
[52] U.S. Cl. ........................ 530/350; 530/327; 530/399; 530/850; 435/70.3; 435/70.4; 435/948; 436/64; 436/517
[58] Field of Search .................................. 530/350, 327, 530/399, 850; 435/70.3, 70.4, 240.21, 948; 436/64, 517

[56] References Cited

U.S. PATENT DOCUMENTS 4,803,163   2/1989   Fahey et al. ............................. 435/68

OTHER PUBLICATIONS

Bowie et al, *Science*, Vol. 297, pp. 1306–1310, Mar. 16, 1990.

Houghten et al, *Vaccines* 86, pp. 21–25, Cold Spring Harbor Laboratories, 1986.

Matsunami et al, Research Communications in Chemical Pathology and Pharmacology, vol. 73, No. 3, pp. 371–374, 1991.

Furui et al, Curr. Chem. Pract. Ser. vol. 65, pp. 235–239, 1993.

Furui et al, *Cancer* vol. 73, No. 4, pp. 1239–1244, Feb. 15, 1994.

Proceedings of the Society for Experimental Biology & Medicine vol. 203, No. 1 May 1993 pp. 117–122 Imai et al "Prolactin Binds to Human Endometrial Fibroblasts and Inhibits Mitogenicity etc." (1993).

Cancer vol. 73, No. 4, Feb. 15, 1994 pp. 1239–1244 Furui et al "A Putative New Proteinous Factor Negative for Stromal Growth" (1994).

*Primary Examiner*—Cecilia J. Tsang
*Assistant Examiner*—Abdel A. Mohamed
*Attorney, Agent, or Firm*—Nixon & Vanderhye

[57] ABSTRACT

A novel cell growth-inhibiting protein is provided. The cell growth-inhibiting protein, obtainable from extract of human uterine endometrial carcinoma, has the amino acid sequence rich in hydrophobic residue at its N-terminal, has a molecular weight of about 68,000 dalton, and is considered to act as a paracrine growth-inhibiting factor in an organism.

6 Claims, 4 Drawing Sheets

*Fig. 4*

```
      1    2    3    4    5    6    7    8    9   10   11   12   13   14
NH2-  -    -    -    -Thr-Gln-Ser-(Trp)-Asp-(Phe)-    -Ser-Gln-   -
```

5,932,700

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 14 amino acids
      (B) TYPE: amino acid
      (D) TOPOLOGY: linear (ii) MOLECULE TYPE: peptide (xi) SEQUENCE DESCRIPTION: SEQ ID NO:1:

```
Xaa Xaa Xaa Xaa Thr Gln Ser Trp Asp Phe Xaa Ser Gln Xaa
1               5                   10
```

PROTEIN INHIBITING THE GROWTH OF HUMAN ENDOMETRIAL FIBROBLASTS

This is a file wrapper continuation of application Ser. No. 08/317,461, filed Oct. 4, 1994, now abandoned.

FIELD OF THE INVENTION

This invention relates to a cell growth-inhibiting protein, which inhibits the growth of human uterine endometrial fibroblast, and thus is effective as a medicament for inhibiting tumor growth and metastases.

PRIOR ART

It is known that many types of tumor cells produce substances that directly or indirectly promote their own growth. It is known that some types of tumor cells produce substances that directly or indirectly inhibit their own growth (Iversen O. H., Adv. Cancer Res. 1991; 57: 413–52).

For example, tumor cells secrete proteinous growth factors into their condition medium when grown in a cell culture (James R., Bradshaw R. A., Annu. Rev. Biochem., 1984; 53: 259–92, Rozengurt E., Science 1986; 234: 161–66, Sporn M. B., Roberts A. B., Nature 1985; 313: 745–47, Bradshaw R. A., Sporn M. B., Fed. Proc. 1983; 42: 2590–91). These tumor cells or co-cultured fibroblasts often express receptors for secreted proteinous growth factors (Sporn M. B., Roberts A. B., Nature 1985; 313: 745–47). Many types of these factors including type α and β transforming growth factors (TGF-α and β), platelet-derived growth factor (PDGF), and bombesin have been known to lead eventually to a mitogenic response of cells.

TGF-β has already been purified to high homogeneity. This factor can sometimes act negatively on the growth of neoplastic cells of either fibroblastic or epithelial cells (Tucker R. F., Shipley G. D., Moses H. L., Holly R. W., Science 1984; 226: 705–07, Tucker R. F., Braum E. L., Shipley G. D., Ryan R. J., Moses H. L., Proc. Natl. Acad. Sci. USA 1984; 81: 6757–61). However, the set of conditions in a cell determining whether the action of TGF-β is positive or negative for the growth is complex and cannot be explained simply by differences in cell types, growth conditions or the concentrations of TGF-β. In addition, it has been suggested that uterine cervical and endometrial carcinomas also synthesize and secrete a putative proteinous growth factor(s) for endometrial fibroblasts (Imai A., Matsunami K., Tamaya T., Obstet. Gynecol. Invest., 1992; 33: 109–13, Imai A., Matsunami K., Iida K., Tamaya T., Biosci. Rep. 1990; 10: 47–53). These growth factors may exhibit their effects by a paracrine or autocrine mechanism, i.e. they may be produced and released in the immediate vicinity of their sites of action.

Such growth promoting or inhibiting substances derived from tumor cells are expected to be useful as pharmaceutical agents, and various studies have been conducted to discover substances capable of effecting cell growth from tumor cells.

SUMMARY OF THE INVENTION

An object of the present invention is to provide a cell growth-inhibiting protein which is capable of inhibiting growth of stromal cells, especially fibroblasts, and eventually inhibiting growth of tumors, in an attempt to contribute to the development of a tumor growth-inhibiting agent. For example, the invention provides a cell growth-inhibiting protein derived from a tumor, uterine endometrial carcinoma.

A further object of the invention is to provide a method for immunologically detecting said protein in a biological sample by using an antibody specific to said protein in order to allow detection of the presence of tumor cells.

BRIEF DESCRIPTION OF THE DRAWINGS

FIG. 4 shows the $NH_2$-terminal 14 amino acids of the cell growth-inhibiting protein purified by Affi-Gel Blue gel chromatography.

DETAILED DESCRIPTION OF THE INVENTION

Figure 1:
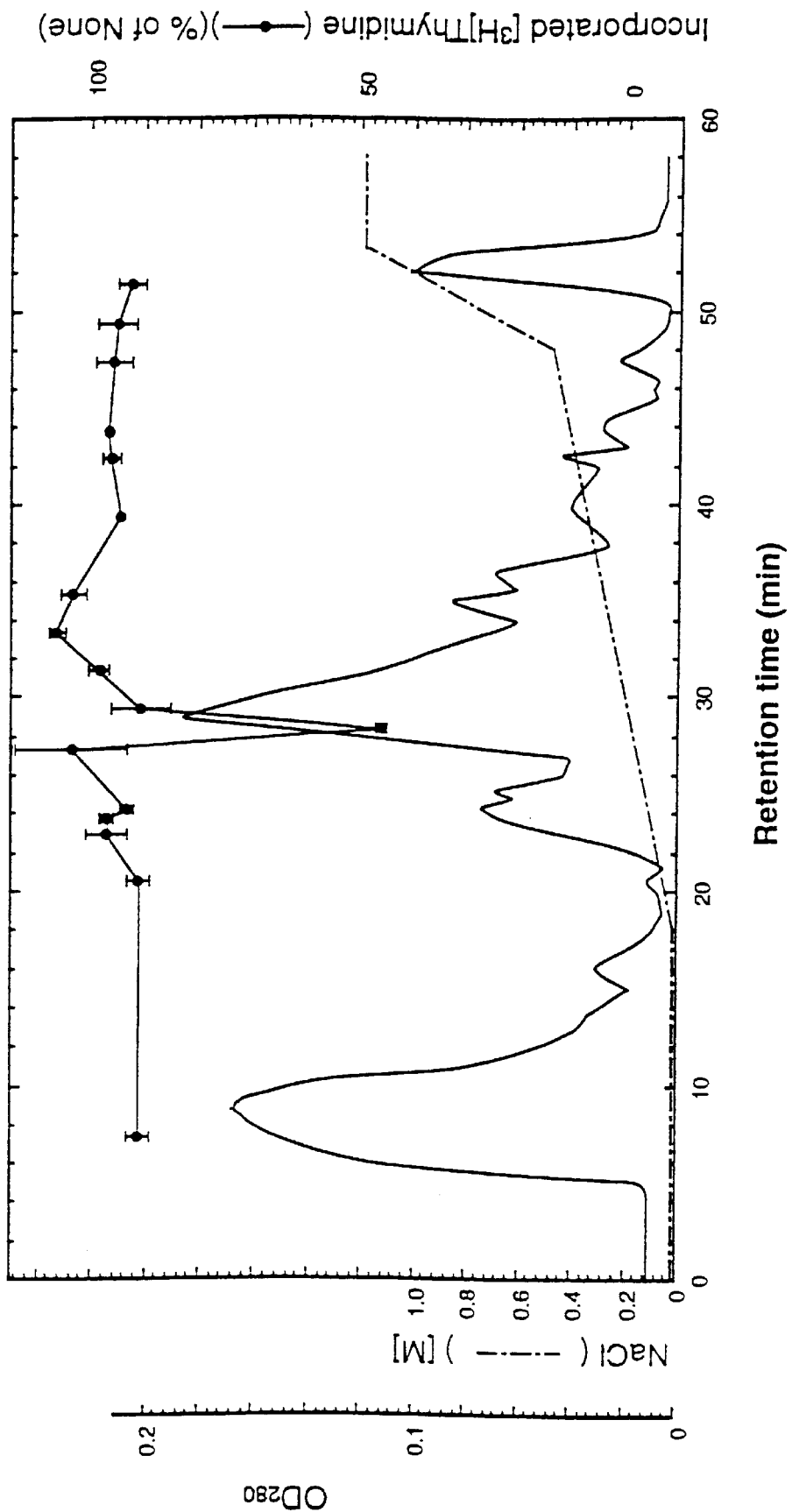
FIG. 1 illustrates the elution pattern, on anion exchange chromatography, of the fraction greater than 10,000 dalton from an endometrial carcinoma extract.

Many factors are considered to relate to tumor cell growth. For one thing, tumor cell growth requires co-growth of surrounding stromal cells. In fact, it is known that tumor cells themselves produce mitogen for surrounding stromal cells. For example, uterine endometrial carcinoma has been reported to synthesize and secrete putative mitogens, which elicit a positive proliferation response in endometrial fibroblasts (Proc. Soc. Exp. Biol. Med. 203: 117–122, 1993).

Recently, the present inventor has found that tumor cells produce growth-inhibiting factors as well as growth-promoting factors. He has thus isolated and purified a protein as one such negative factor to accomplish the present invention.

The cell growth-inhibiting protein of the present invention has the following characteristics:

a) It is a paracrine growth-inhibiting factor of a novel class, which inhibits [$^3$H]thymidine uptake by fibroblasts, such as, stromal fibroblasts of uterine endometrial carcinoma, in an assay of the incorporation of [$^3$H]thymidine uptake.

b) It shows substantially the same molecular weight at about 68,000 dalton, as determined by Gel-filtration and SDS-polyacrylamide gel electrophoresis.

c) It is hydrophilic as a whole, but has the amino acid sequence of SEQ ID No:1 which is rich in hydrophobic residues, at its $NH_2$-terminus.

d) It can be distinctly separated from albumin by Affi-Gel blue gel chromatography.

The cell growth-inhibiting protein of the present invention has been found in the tissue of uterine endometrial carcinoma. However, the present inhibiting protein is expected to be found in other tumor tissues or normal tissues. Further, it will be present in cell cultures (in vivo or in vitro) of such tissues. The extraction and the purification of the present inhibiting protein using said tissues or cells as starting materials, can be performed as follows, for example:

A sample of tissues or cells expected to contain the inhibiting protein, is homogenized in an appropriate liquid, for example, in a buffer at a neutral pH such as phosphate-buffered saline (PBS), preferably at low temperature. Unsoluble substances are removed from the homogenate by appropriate means such as high-speed centrifugation, and the supernatant can be obtained. The supernatant is purified by an appropriate combination of molecular size exclusion filtration, anion exchange chromatography, gel filtration and albumin exclusion by for example, Affi-Gel blue gel chromatography. Electrophoresis and any other conventional methods in the field of protein purification can be applied for further purification, if necessary.

In the course of the above purification steps, fractions containing the present inhibiting protein can be monitored based on the ability of inhibiting [$^3$H]thymidine incorporation by primary culture or established cell line of fibroblasts separated from uterine endometrium.

The purification procedure will yield a substantially pure protein of about 68,000 dalton, which represents a purification by about 20,000-fold compared to the supernatant of the original homogenate of cells or tissue. The protein will evoke 90%-inhibition of [$^3$H]thymidine incorporation into uterine endometrial fibroblasts in nanomolar range concentration or less. The present protein is a novel protein, having the unique amino acid sequence of SEQ ID NO:1 rich in hydrophobic amino acid residues, at its N-terminus.

The invention provides a cell growth-inhibiting protein comprising the amino acid sequence in its N terminus

```
Xaa Xaa Xaa Xaa Thr Gln Ser Trp Asp Phe Xaa Ser Gln Xaa
            5                          10
``` in which each Xaa represents an amino acid that has not been identified. N-terminal amino acid sequencing yielded an identical and unambiguous sequence, as shown in FIG. 4.

The present invention further relates to a method of immunologically detecting said protein in a biological sample immunochemically by using an antibody to said protein. That is, the presence of uterine endometrial carcinoma or the like can be diagnosed indirectly by detecting the cell growth-inhibiting protein of the present invention in the biological sample.

An antibody useful for the detecting method of the present invention can be any antibody which reacts specifically with said protein, i.e. either a polyclonal antibody or a monoclonal antibody can be employed. These antibodies can be prepared easily by those skilled in the art according to a conventional method.

Methods of immunologically detecting a protein in a biological sample immunochemically, are also well-known and those skilled in the art can select an appropriate method. Among these methods, a fluorescent antibody method, ELISA and radioimmuno assay can be mentioned as examples.

The cell growth-inhibiting protein of the present invention consistently directs the reaction towards growth inhibition of uterine endometrial fibroblast in the interaction between uterine endometrial carcinoma and fibroblasts. Therefore, the cell growth-inhibiting protein of the present invention can be administered to tumor patients, especially with uterine endometrial carcinoma, in order to suppress growth of surrounding stromal cells, especially fibroblasts, and eventually to suppress growth of said tumor cells themselves.

The invention will be explained in more detail by way of the following non-limiting examples.

Method for Determining Growth Inhibiting Activity
A. Preparation of Human Endometrial Fibroblasts Specimens of normal endometria were obtained from patients undergoing elective hysterectomy for uterine leiomyoma or dilatation and curettage as a screening test for carcinoma. The removed tissues were trimmed and washed with Hanks balanced salt solution (HBSS), and subsequently treated for 1.5 hour at 37° C. with 0.25% collagenase (type I, Sigma) in HBSS solution, as previously described (Imai A., Matunami K., Tamaya T., Obstet. Gynecol. Invest. 1992; 33: 109–13, Imai A., Matsunami K., Iida K., Tamaya T., Biosci. Rep., 1990; 10: 47–53, Imai A., Furui T., Matsunami K., Takahashi K., Tamaya T., Proc. Soc. Exp. Biol. Med. 1993; 203: 117–122). The cell suspension was filtered through nylon mesh to remove tissue fragments, cell debris and fibers. The filtrate was then centrifuged and washed with HBSS. The cells in the pellet were resuspended and incubated in modified minimum essential medium, Eagles (MEM) supplemented with 10% fetal bovine serum (FBS). After several days of incubation, nonadherent cells were removed, and the fibroblasts were grown as a monolayer. The growth medium was changed every second day until confluence was reached, and these were maintained in the above medium as a stock culture. One stock culture was prepared from one patient, and the experiments were always performed using three stock cultures. No significant difference was detected between fibroblasts from secretory phase-endometrium and in the cells from proliferative phase-endometrium in the assay.

B. [$^3$H]Thymidine Incorporation Into Endometrial Fibroblasts

DNA synthesis was assayed by measuring the incorporation of [6-$^3$H]thymidine (1.11 TBq/mmol, New England Nuclear) into the trichloroacetic acid (TCA)-insoluble fraction. Before experimentation, the confluent cells were seeded into plastic 24-well plates at a density of $1.0 \times 10^5$ cells/cm$^2$. At confluence, monolayer cultures were preincubated in MEM with 1% FBS for 2 days, and submitted to concurrent exposures to various agents to be tested at 37° C. [$^3$H]Thymidine incorporation was examined by a continuous or a 2-hour pulse labeling with 1 $\mu$Ci/well, and uptake was quenched by aspiration of media. The cells were washed with ice-cold 0.5% TCA and washed three times by centrifugation (400×g, 5 min). The radioactivity associated with acid-insoluble material at the bottom of the tube was counted.

Example 1

A. Preparation of Extract from Human Uterine Endometrial Carcinoma

Uterine endometrial carcinomas were placed in ice-cold phosphate-buffered saline (PBS) immediately after surgical removal. These tumor samples were washed, and immediately used or stored in liquid nitrogen. Specimens found histologically to represent well-differentiated adenocarcinoma were submitted to separate experiments. After washing at 0–4° C. with PBS, a volume of homogenizing buffer (0.25M sucrose, 1 mM ethyleneglycol tetraacetic acid (EGTA), 10 mM HEPES, pH 7.4) was added equal to 4–5 times the volume of the removed tissue. Routinely 2 to 5 g tissue was subsequently homogenized at 0–4° C. using a teflon homogenizer. The homogenate was then centrifuged at 100,000×g for 1 hour and the resulting supernatant ("extract") was stored in liquid nitrogen. Protein content was determined by the method of Lowry et al. with bovine serum albumin (BSA) as a standard (Lowry O. H., Rosenbrough N. J., Farr A. L., Randall R. J., J. Biol. Chem., 1951; 193: 265–75).

B. Molecular Size Exclusion Filtration

The crude uterine endometrial carcinoma extract (5 to 15 ml) was fractionated by ultrafiltration with a membrane of 10,000 dalton molecular weight exclusion limits (Centriprep-10 or Centricon-10, Amicon), according to the manufacturer's instructions. The solutes with molecular weight above 10,000 dalton suppressed proliferation of the endometrial fibroblasts as indicated by [$^3$H]thymidine incorporation to approximately 20% of control (Table 1).

On the other hand, the solutes containing lower molecular weight (below 10,000 dalton) were stimulatory (data not shown). The active fractions which inhibit proliferation of the endometrial fibroblasts were pooled. The activity positive fractions were pooled. The minimum amount of activity required for pooling was 30% inhibition of [$^3$H]thymidine incorporation when compared to control; 4 of 15 specimens had less activity.

In Table 1, human serum was obtained from cubital venous blood of healthy female donors, and allowed to clot at 37° C. for 2 hours followed by brief centrifugation. Serum was then poured off the clot and used.

C. Anion Exchange Chromatography

In order to continue the purification of the activity positive fraction from the molecular size exclusion filtration, a chromatography was performed with a HPLC apparatus using an anion exchange Mono Q HR columns (10×1 cm, Pharmacia) in 0.02M HEPES, pH 7.4, at 4° C. The growth inhibiting factors were eluted with a linear gradient from 0 to 1.0M NaCl in 0.02M HEPES at a flow rate of 2 ml/min. Fractions were collected (2 min) and their growth-inhibiting activity was examined. FIG. 1 shows a representative elution pattern of three separate experiments that gave similar results. In the figure, the inhibiting activity for each fraction is expressed in percentage the [$^3$H]thymidine incorporation in the presence of the fraction compared to that in absence thereof. The value represents means±SD. Apparently from the figure, only the component(s) present in the 0.18–0.20M NaCl eluate inhibited [$^3$H]thymidine uptake by endometrial fibroblasts. The fractions containing growth-inhibiting activity were pooled and termed the growth-inhibiting activity gel filtration pool. The activity positive fractions were frozen-dried in a Speed-Vac apparatus (Kubota, Japan). Dried samples were then reconstituted and immediately submitted to next purification step.

D. Gel Filtration

Figure 2:
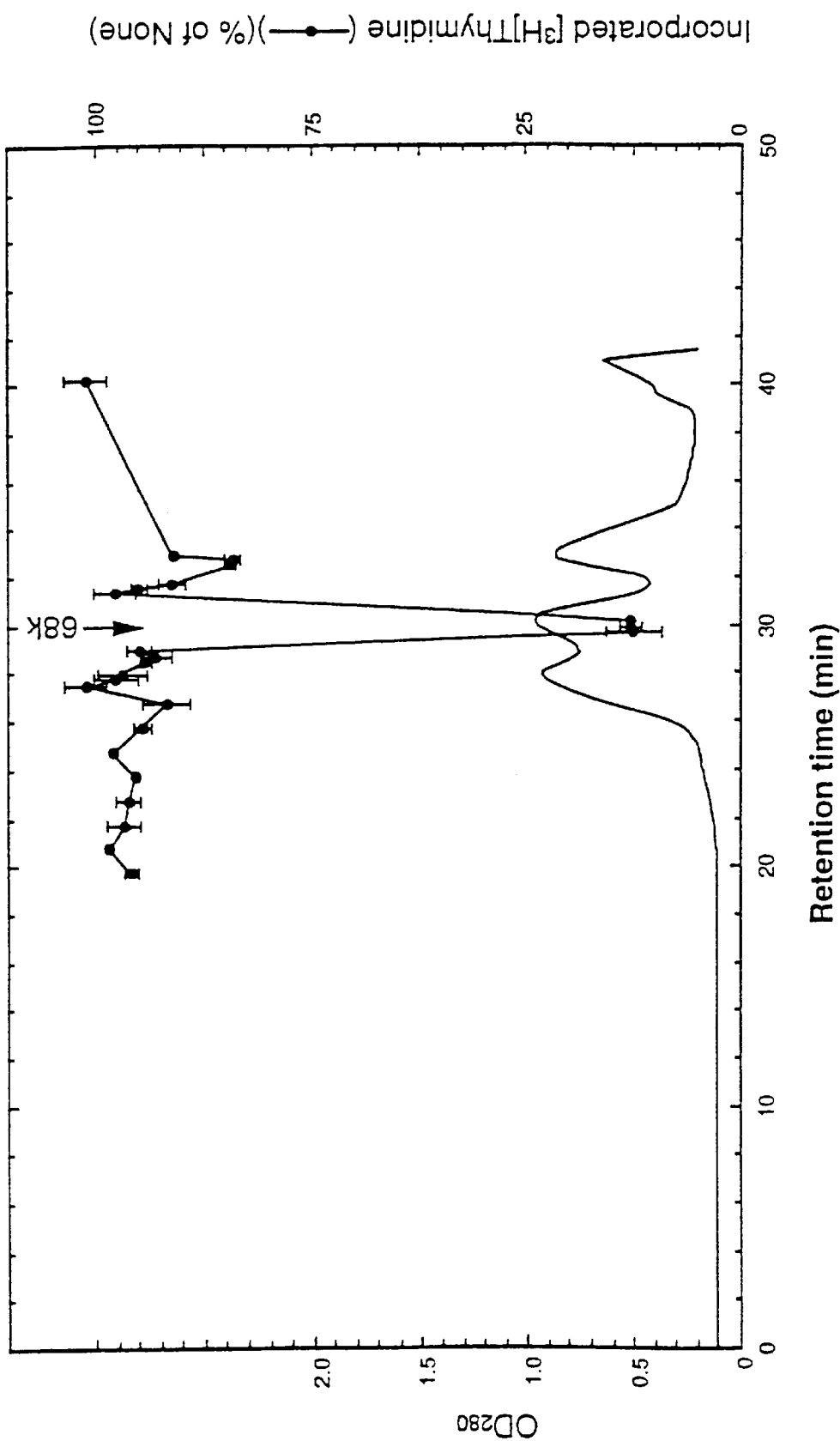
FIG. 2 illustrates the separation pattern, on gel filtration, of cell growth inhibiting activity positive fractions from the anion exchange chromatography.

Gel filtration was performed on a Superose 12 HR (1×30 cm, Pharmacia). The column was equilibrated in 20 mM HEPES, 150 mM NaCl, pH 7.4. The reconstituted samples were loaded and eluted at 0.5 ml/min with a buffer consisting of 20 mM HEPES, 150 mM NaCl, pH 7.4. Protein elution was monitored at 280 nm. Fractions were collected (1 min), and submitted to the growth assay. Standardization of the column for molecular weight was done with BSA (67,000 dalton), ovalbumin (42,000 dalton) and chymotrypsinogen (25,000 dalton). FIG. 2 shows a representative gel filtration pattern. From the figure, the substance(s) of approximately 68,000 molecular mass apparently exhibited inhibitory activity. However, an identical retention time of the activity to the serum albumins may indicate the possibility that the activity appeared to be due to serum albumin present in the same fractions. The Affi-Gel blue gel procedure was used to separate the growth-inhibiting activity from the albumins as described below.

E. Affi-Gel Blue Gel Chromatography

Affi-Gel blue gel, a dye affinity support, was therefore used for albumin removal from the samples, based on the selective interaction between albumin and blue F-3-GA dye (Travis J., Bowen J., Tewksbury D., Johnson D., Pannel R., Biochem J., 1976; 157: 301–06, Marshall J J., J. Chromatogr. 1970; 53: 379–380). The fractions were applied to an Econo-Pac blue cartridge packed with Affi-Gel blue gel (Bio-Rad) in 0.02M Na$_2$HPO$_4$, pH 7.1 at 40° C., according to the manufacturer's recommendation. The column was eluted with 10–15 ml of 0.02M Na$_2$HPO$_4$ at a flow rate of 1 ml/min. The eluting fractions were collected (1 min) and concentrated to the starting volume by ultrafiltration with a Centriprep-10 as described above. The bound proteins including albumins were eluted by washing the cartridge with 10–20 ml of 1.4M NaCl, 0.02M Na$_2$HPO$_4$, pH 7.1 at a flow rate of 1 ml/min.

Figure 3:
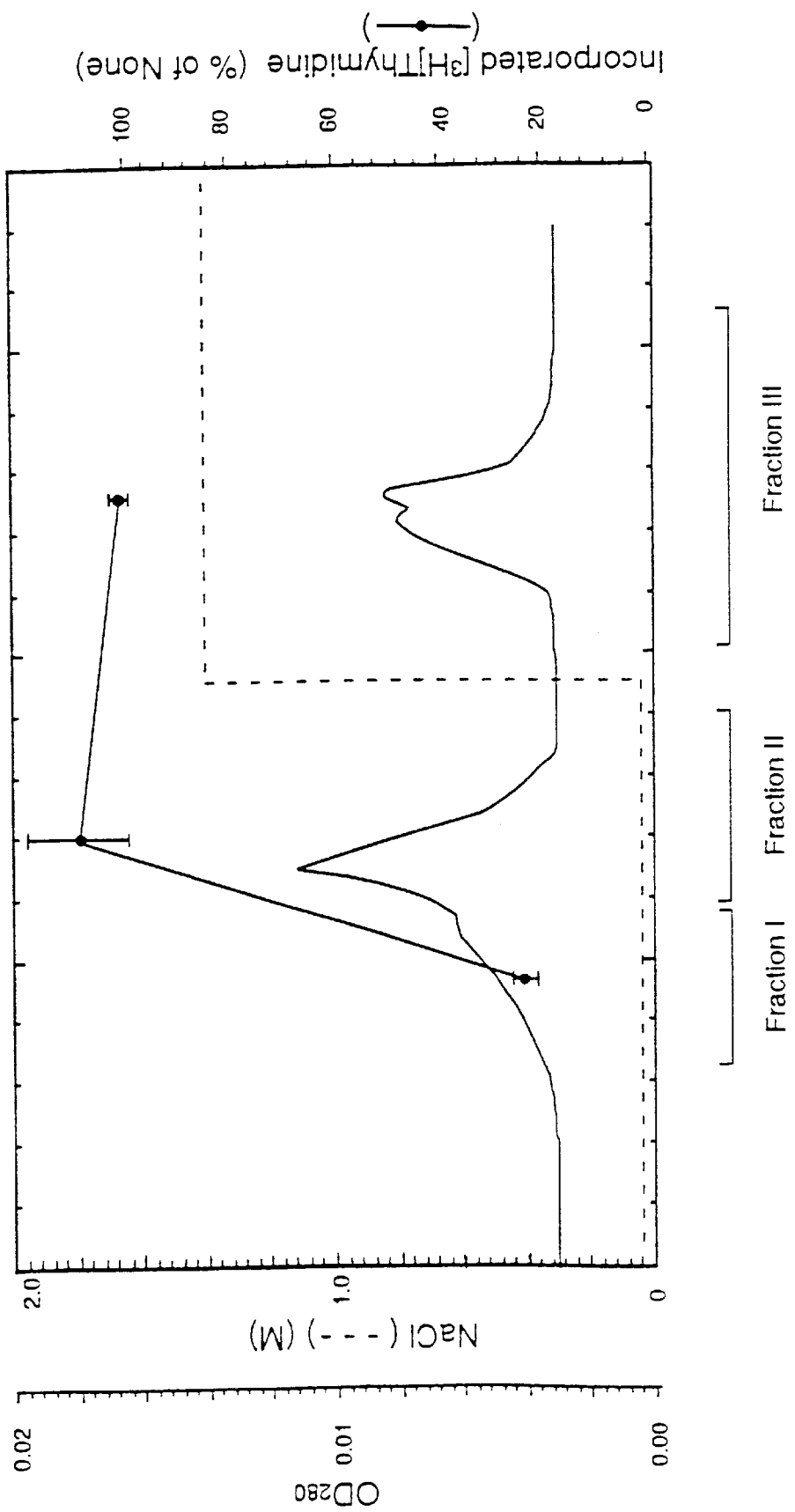
FIG. 3 illustrates purification pattern, on Affi-Gel Blue gel chromatography, of cell growth inhibiting activity positive fractions from the gel filtration.

FIG. 3 shows a representative chromatography pattern of two separate experiments. No inhibitory activity was eluted with loosely bound albumin fraction 2 and the strongly bound albumin fraction 3 from Affi-Gel blue gel. In contrast, fraction 1 containing no albumin was always active at 20 to 30 thousand-fold dilution. It is important to note that fractions 2 and 3 contained albumin and no inhibitory growth activity was detectable in these two fractions. This observation implies that the inhibitory activity and the albumin effect are distinct activities.

The level of the activity present in these samples for each purification step was determined with the growth activity (Table 1). The amount of protein required to induce the similar inhibitory action was reduced 20,000-fold in specific activity.

TABLE 1

Quantitation of the growth-inhibiting activity in purification step

| Step | Protein (mg) | Purification (fold) | [$^3$H]Thymidine uptake (dpm × 10$^{-3}$) (%) |
|---|---|---|---|
| None | | | 8.5 (100) |
| Crude extract | 20,000 | 1 | |
| Size exclusive filtration | 6,200 | 3.2 | 1.5 (18.2) |
| Mono Q | 240 | 83.3 | 1.1 (12.9) |
| Gel filtration | 35.5 | 563.3 | 1.6 (18.8) |
| Affi-Gel blue gel | 0.88 | 22,727 | 1.5 (18.2) |
| Human serum | | | 9.2/1 µg |

All fractions were arranged to the starting crude extract volume (2 ml) and an aliquot (1 µl) was applied to the endometrial fibroblast for monitoring the growth-inhibiting activity.

F. Electrophoresis

Proteins were separated by 10% polyacrylamide gel electrophoresis in sodium dodecyl sulfate (SDS) essentially as described by Laemmli (Laemmli W. K., Nature 1970; 227: 680). A single protein band of 68,000 molecular mass was confirmed.

G. Partial NH$_2$-terminal Sequence Determination

The growth-inhibiting factor, purified as described above, was analyzed by Edman-degradation using an Applied Biosystems pulse-liquid phase Sequencer equipped with on-line HPLC identification of PTH-amino acids, according to standard procedures. NH$_2$-terminal amino acid sequencing of the factor yielded identical and unambiguous sequence, as shown in FIG. 4; there was no homology to the sequence of ready known protein molecule. Shaded are nonpolar amino acids.

What is claimed is:

1. A cell growth-inhibiting protein comprising SEQ. ID NO: 1, wherein said protein has 68 kDa molecular mass as determined by SDS-polyacrylamide gel electrophoresis and gel filtration, and has growth-inhibiting activity to human uterine endometrial fibroblasts.

2. The cell growth-inhibiting protein according to claim 1, wherein said protein is derived from uterine endometrial carcinoma cells.

3. The cell growth-inhibiting protein according to claim 1, wherein said protein inhibits about 90% of thymidine uptake by stromal fibroblasts from uterine endometrium at a nanomolar concentration.

4. A method of detecting the presence of tumor cells in a tissue specimen suspected of having a tumor, comprising the steps of:

(a) providing a tissue specimen which is suspected of having a tumor;

(b) reacting the tissue specimen with an antibody specific to a cell growth-inhibiting protein comprising SEQ ID NO:1, wherein said protein has a molecular mass of 68 kDa as determined by SDS-polyacrylamide gel electrophoresis and gel filtration, and has a growth-inhibiting activity to human uterine endometrial fibroblasts; and (c) determining the presence of a tumor cell in said tissue specimen by an antibody-antigen reaction observed between said antibody and the protein in said tissue specimen.

5. The method according to claim 4, wherein said protein is derived from uterine endometrial carcinoma cells.

6. The method according to claim 4, wherein said protein inhibits about 90% of thymidine uptake by stromal fibroblasts from uterine endometrium at a concentration in the order of nanomolar or less.

\* \* \* \* \*